(12) United States Patent
Castañeda

(10) Patent No.: US 7,299,561 B2
(45) Date of Patent: Nov. 27, 2007

(54) GAUGE SYSTEM FOR USE IN IMPLANTATION OF A FRACTURE FIXATION DEVICE

(75) Inventor: Javier Castañeda, Miami, FL (US)

(73) Assignee: DePuy Products, Inc., Warsaw, IN (US)

( * ) Notice: Subject to any disclaimer, the term of this patent is extended or adjusted under 35 U.S.C. 154(b) by 659 days.

(21) Appl. No.: 10/686,285

(22) Filed: Oct. 15, 2003

(65) Prior Publication Data

US 2005/0085825 A1  Apr. 21, 2005

(51) Int. Cl.
*A61B 5/103* (2006.01)
(52) U.S. Cl. ....................................... 33/512
(58) Field of Classification Search ................. 606/62, 606/96, 64, 80, 86, 98, 102, 53; 408/241 G; 33/512
See application file for complete search history.

(56) References Cited

U.S. PATENT DOCUMENTS 4,341,206 A * 7/1982 Perrett et al. ................ 606/80
5,013,318 A * 5/1991 Spranza, III ................ 606/102
5,122,146 A * 6/1992 Chapman et al. ........... 606/102
5,409,493 A * 4/1995 Greenberg .................... 606/96
5,458,654 A 10/1995 Tepic
6,527,775 B1 3/2003 Warburton
6,729,037 B2 * 5/2004 White ......................... 33/755

OTHER PUBLICATIONS

Article: "The Hand Sourcebook" (Instruments for Surgeons) by K Medic; dated 2002; 5pgs.
Article: SCS/D "Distal Radius Plate System"; Avanta Orthopaedics 1997; 6 pgs.

* cited by examiner

*Primary Examiner*—Eduardo C Robert
*Assistant Examiner*—Anitza M San Miguel
(74) *Attorney, Agent, or Firm*—Gordon & Jacobson, PC

(57) ABSTRACT

A drill guide includes a window and graduated indicia corresponding to a scale provided along a side of the windows. A gauge for use therewith includes a handle, a shaft having a reference mark thereon, and an end portion. The end portion is slightly angled relative to the remainder of the shaft and is spring-like. The end portion includes a rounded tip which ensures that the gauge rides smoothly in and out of drilled bone and bore, and an angled upper catch that allows a user to retrieve the gauge without chipping bone.

7 Claims, 11 Drawing Sheets

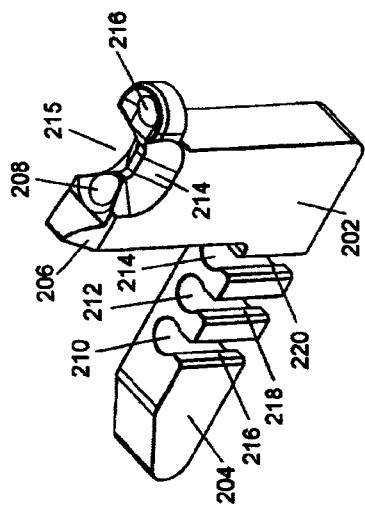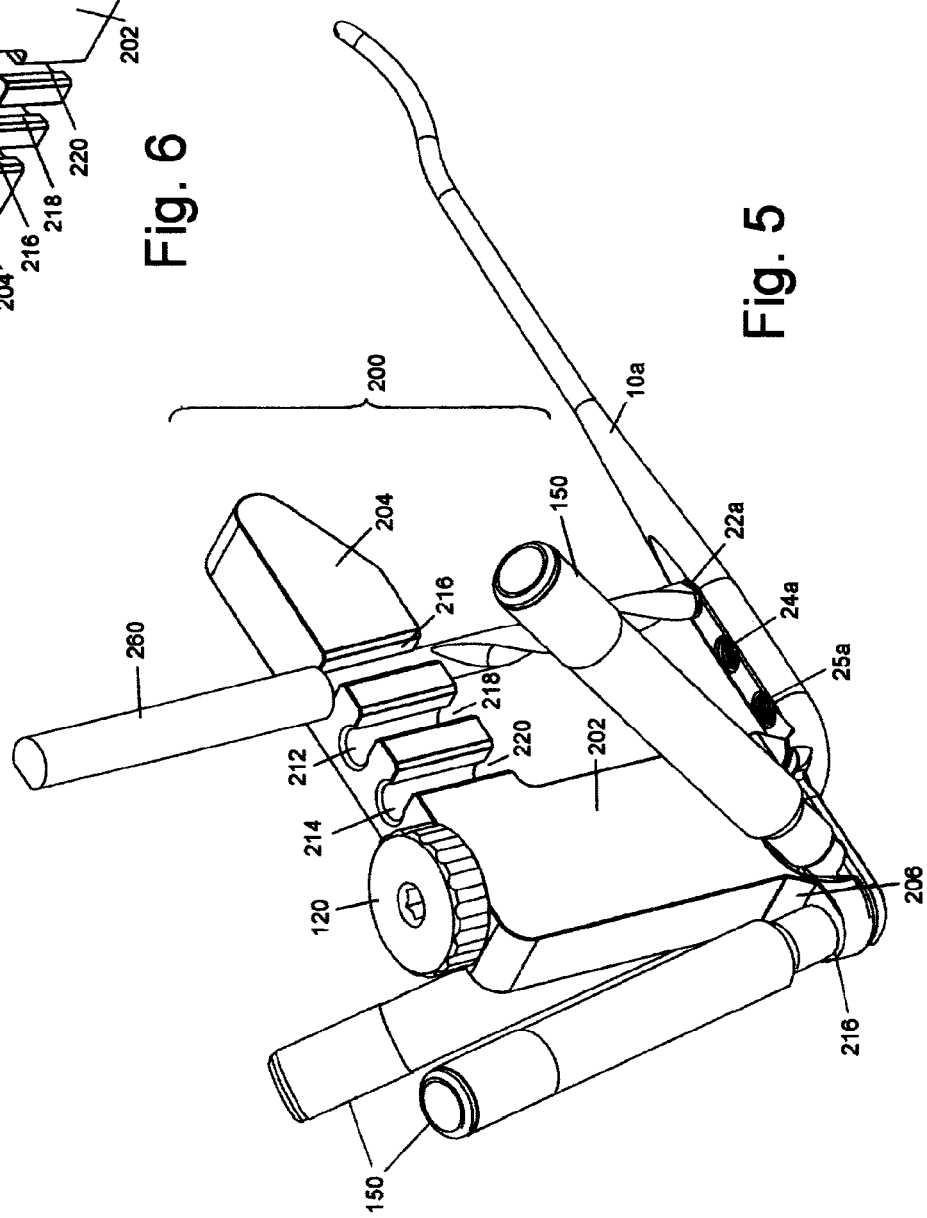

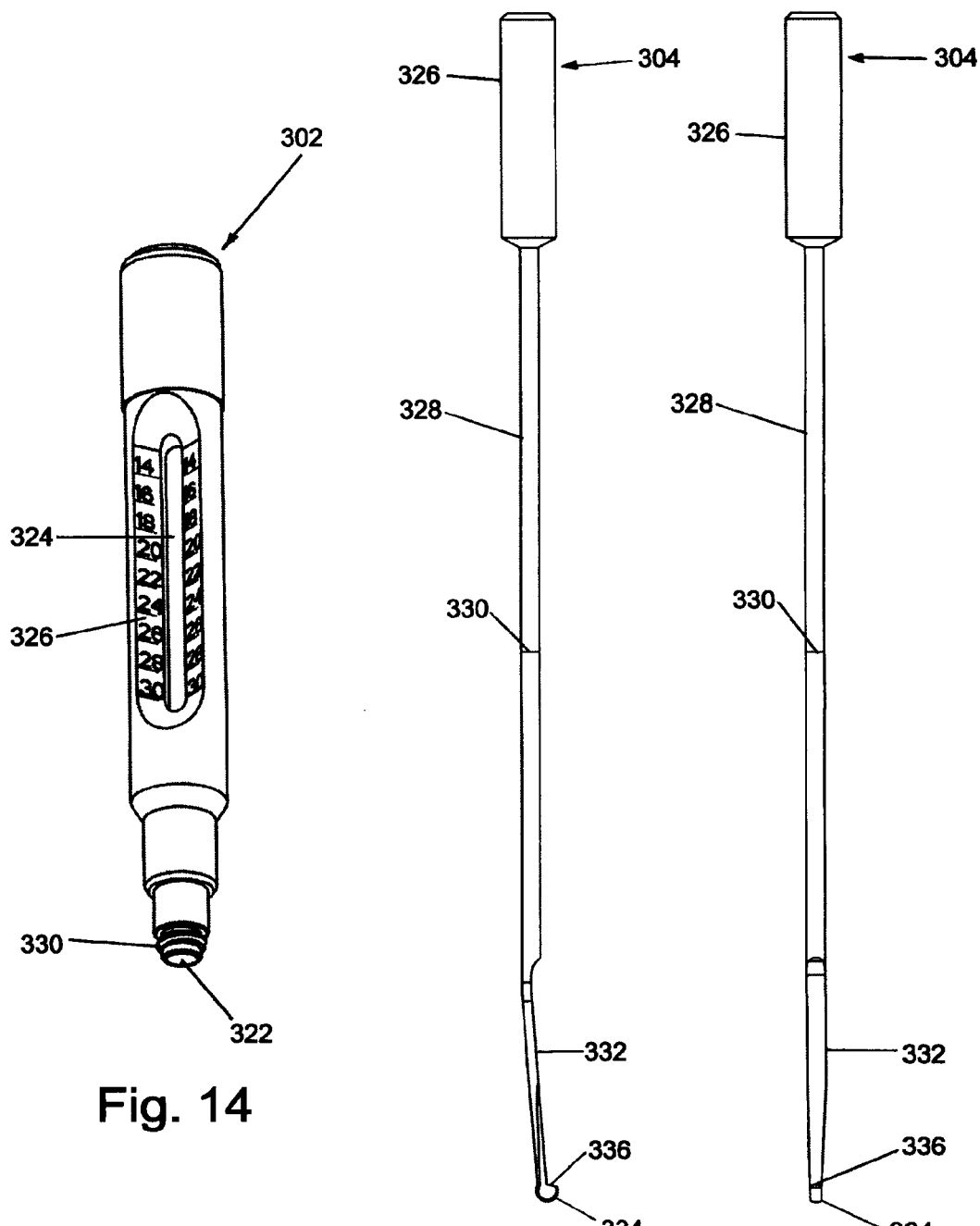

GAUGE SYSTEM FOR USE IN IMPLANTATION OF A FRACTURE FIXATION DEVICE

BACKGROUND OF THE INVENTION

1. Field of the Invention

This invention relates broadly to surgical devices. More particularly, this invention relates to tools for implanting fracture fixation devices.

2. State of the Art

Severe long bone fractures are often treated with plating. In plating, a relatively large incision is made at the location of the fracture, musculature and tendons are displaced from the bone to expose the bone surface, and a bone plate is fixedly attached to one or more pieces of the fractured bone in a manner which, ideally, supports and stabilizes the fracture for healing. Due to the relatively invasive nature of the procedure required to implant the plate, plating is generally reserved for fractures which cannot be treated with a less invasive method of immobilization.

Less complicated fractures are often treated with casting or wires. However, such conservative treatment may not provide the stabilization and support necessary for desirable recovery. Yet, the operative procedure of plating is often too invasive for the relative non-severity of the fracture. Moreover, conventional plating can result in tendon irritation and skin necrosis, and may require extensive periosteal stripping in order to apply the plate on the bone surface. As such, many of the less displaced fractures, and particularly metaphyseal fractures (fractures at the end of the long bones), remain undertreated.

By way of example, a Colles' fracture, which results from compressive forces being placed on the distal radius bone, and which causes backward displacement of the distal fragment and radial deviation of the hand at the wrist, is treated with a dorsal plate when there is a significant degree of displacement. However, a less-displaced Colles' fracture is commonly undertreated due to the hesitancy of physicians to prescribe operative and invasive treatment. If not properly treated, such a fracture results in permanent wrist deformity. It is therefore important to align the fracture and fixate the bones relative to each other so that proper healing may occur.

More recently, minimally invasive fixation devices have become available for treatment of wrist fractures. Particular devices, such as that described in co-owned and co-pending U.S. Ser. Nos. 10/159,611, filed May 30, 2002, and Ser. No. 10/315,787, filed Dec. 10, 2002, include an intramedullary portion which is secured within or to the cortical bone with cross-fastened screws. In addition, these fixation devices include a plate portion into which a plurality of bone pegs are secured. Pegs of an appropriate length are oriented in relatively oblique angles relative to each other to stabilize the subchondral bone fragments relative to the plate portion.

It is therefore necessary to provide to the surgeon a tool facilitating longitudinally displaced holes drilled through the cortical bone in alignment with the longitudinally displaced screw holes in the intramedullary portion of the fixation device so that the fastening screws may be inserted through the bone and the screw holes. In addition, it is also preferable to provide tools which are adapted to drill holes into the subchondral bone for the pegs in the desired oblique directions. In addition, tool must be provided for selecting pegs of an appropriate length.

SUMMARY OF THE INVENTION

It is therefore an object of the invention to provide a jig assembly for assistance in implantation of a fixation device relative to a fractured bone.

It is another object of the invention to provide a jig assembly for a fixation device designed to treat metaphyseal fractures.

It is a further object of the invention to provide a jig assembly which provides proper alignment between longitudinally displaced holes drilled in bone and corresponding openings in an intramedullary portion of the fixation device such that fasteners can be inserted through the holes and openings.

It is an additional object of the invention to provide a jig assembly which facilitates drilling of axially aligned holes through peg holes in a plate of a fixation device and through metaphyseal bone.

It is yet another object of the invention to provide a jig assembly which properly and easily measures drilled hole depth.

It is also an object of the invention to provide a jig assembly which prevents potential tissue damage by the drill.

It is yet another object of the invention to provide a jig assembly which stops the drill at a precise distance relative to a jig so that an implant within the bone below is not damaged, even though the radius bone into which the implant is positioned may have a varying thickness along its length and different thicknesses in different patients.

It is also an object of the invention to provide a depth gauge for a jig assembly which easily and accurately determines the length of pegs which should be used with the fixation device.

In accord with these objects, which will be discussed in detail below, a jig assembly for a fixation device is provided.

In order to more easily understand the jig assembly, it is helpful to understand that the jig assembly is adapted for use with an orthopedic implant such as the fixation devices described in detail in U.S. Ser. Nos. 10/159,611, filed May 30, 2002, and Ser. No. 10/315,787, filed Dec. 10, 2002, which are hereby incorporated by reference herein in their entireties. In brief, such fixation devices include a proximal intramedullary nail portion and a distal supra-metaphyseal plate portion which is horizontally and vertically offset relative to the nail portion by a neck portion. The nail portion includes two or more threaded screw holes, and the plate portion has a low, narrow profile and includes three longitudinally displaced peg holes, each of which is adapted to orient a peg in a different orientation from the others. The plate and/or neck portions also include a threaded locking hole.

With the fixation devices in mind, the jig assembly includes a jig having an elevated first portion in alignment over the screw holes of the intramedullary portion of the fixation device, and a second portion seatable on the plate portion of the fixation device. The first portion includes longitudinally displaced holes or slots, as described further below, to longitudinally align a drill with the screw holes in the intramedullary portion of the fixation device. The second portion includes openings in axial alignment with the peg holes. The jig also includes a hole over the threaded locking hole in the fixation device, and the assembly includes a locking screw adapted to extend through the hole and couple the jig to the fixation device at the threaded locking hole.

According to one embodiment of the invention, the first portion of the jig includes a plurality of longitudinally displaced holes, a first sleeve adapted to be received in any of the holes, and a second sleeve sized to be received within the first sleeve, but removable therefrom. The second sleeve is diametrically sized to guide a rotary drill to cut the bone cortex, and the first sleeve is diametrically sized to receive the head and body of a cortical screw adapted to engage within the screw holes of the intramedullary portion of the fixation device. The sleeve-in-sleeve structure may be positioned in each of the holes of the first portion of the jig to guide the drill for each of the cortical screw holes.

According to another embodiment of the invention, the first portion of the jig includes a plurality of longitudinally displaced holes, and slots which provide lateral entrance into each of the holes. A drill may be side loaded into holes via the slots. A bridged-sleeve is optionally provided for use with the holes, and (1) accounts for changing or different thicknesses in the bone (2) more stably guides the drill, and (3) prevents the drill from catching and tearing tissue near the entrance to the drilled cortical bone.

The jig assembly further includes a drill guide having a threaded end which is positionable within the openings in the second portion of the jig and threadably engageable within the peg holes. A single drill guide may be moved from one peg hole to the next to drill the required holes. The drill guide preferably includes a depth gauge for measuring the depth of a drilled hole and determining an appropriate size of bone peg for use with the fixation device.

Additional objects and advantages of the invention will become apparent to those skilled in the art upon reference to the detailed description taken in conjunction with the provided figures.

BRIEF DESCRIPTION OF THE DRAWINGS

FIG. 5 is a perspective view of another embodiment of a jig assembly according to the invention coupled to another embodiment of a fracture fixation system;

FIG. 6 is an inverse perspective view of the jig of the jig assembly of FIG. 5;

FIG. 14 is a perspective view of another embodiment of a drill guide according to the invention, with a view 180° about the drill guide appearing the same;

FIG. 15 is a side elevation of a gauge according to invention;

FIG. 16 is a side elevation of the gauge according to the invention, rotated 90° relative to FIG. 15.

DETAILED DESCRIPTION OF THE PREFERRED EMBODIMENTS

Figure 1:
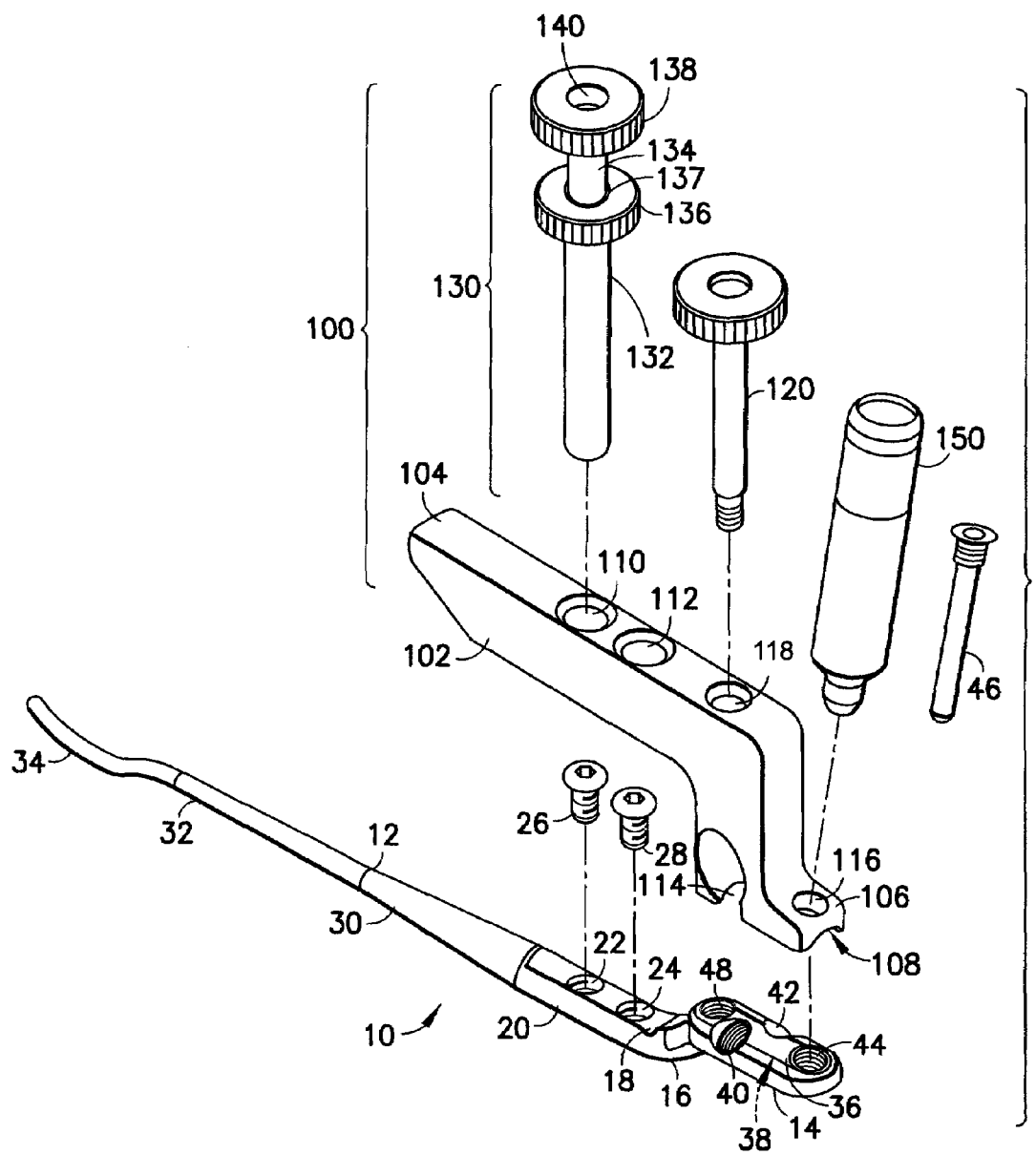
FIG. 1 is an exploded perspective view of a jig assembly and fracture fixation system according to the invention.

In accord with these objects, which will be discussed in detail below, a jig assembly 100 for a fracture fixation device 10 is shown.

In order to provide context for the features and use of the jig assembly 100, it is helpful to first understand the type of fracture fixation devices for which the jig assembly is intended. Similar fracture fixation devices 10 are described in detail in U.S. Ser. No. 10/159,611, filed May 30, 2002, and Ser. No. 10/315,787, filed Dec. 10, 2002, which are hereby incorporated by reference herein in their entireties. In brief, the fixation device 10, which is slightly modified from the devices described in the incorporated specifications and may include inventive features relative thereto, includes a proximal intramedullary nail portion 12 and a distal suprametaphyseal plate portion 14 which is horizontally and vertically offset relative to the nail portion by a neck portion 16. The neck portion 16 may include a notch 18 to facilitate coupling of the jig assembly 100, as described in more detail below. The nail portion 12 includes a relatively rigid section 20 provided with two or more threaded screw holes 22, 24 for cortical screws 26, 28, a tapered section 30, and a relatively stiff, but less rigid end section 32 formed with a curve 34 to facilitate entry into the medullary canal of a bone, e.g., the radius bone. The plate portion 14 has a low, narrow profile, preferably with a convex upper surface 36 and a concave undersurface 38, and includes three longitudinally displaced peg holes 40, 42, 44, each of which is adapted to orient a peg, e.g., peg 46, in a different orientation from the others. The plate and/or neck portions 14, 16 also include a threaded locking hole 48.

With the fixation device 10 in mind, the jig assembly 100 includes a jig 102 having an elevated first portion 104 in alignment over the rigid portion 20 of the intramedullary nail portion 12 of the fixation device 10, and a second portion 106 having a concave lower surface 108 which is stably seatable on the upper convex surface 36 of the plate portion 14 of the fixation device 10. The first portion 104 includes longitudinally displaced guide holes 110, 112 aligned with the screw holes 22, 24 of the fixation device 10. The second portion 106 includes openings 114, 116 (and another not shown) which provide access to peg holes 40, 42, 44. The jig 102 also includes a hole 118 in alignment with the threaded locking hole 48 of the fixation device 10.

Figure 2:
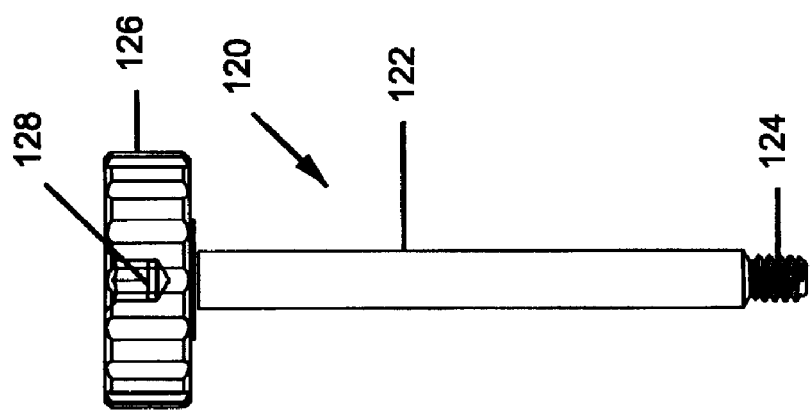
FIG. 2 is a side elevation view of a locking screw of the jig assembly of the invention.

A locking screw 120 extends through the hole 118 and couples the jig 102 to the fixation device 10. More particularly, referring to FIG. 2, the locking screw 120 includes a shaft 122 having a threaded end 124 sized to engage the locking hole 48 and a handle 126 at an opposite end thereof for manually rotating the locking screw into engagement. The locking screw 120 preferably also includes a hex or square driver opening 128 for mechanically rotating the locking screw 120 to lock the jig 102 relative to the fixation device 10.

Referring back to FIG. 1, the jig assembly 100 further includes a sleeved drill guide 130 comprising an outer first sleeve 132 adapted to be received in any of guide the holes 110, 112, and an inner second sleeve 134 sized to be received within the first sleeve 132, but removable therefrom. The second sleeve 134 includes a handle 136 for manual insertion and removal into the guide holes 110, 112, and a bore 137 diametrically sized to guide a rotary drill to cut the bone cortex. The first sleeve includes a handle 138 for manual insertion into and removal from the second sleeve, and a bore 140 diametrically sized to receive the head and body of the cortical screws 26, 28 which are adapted to engage within the screw holes 22, 24 of the intramedullary portion of the fixation device 10.

Figure 4:
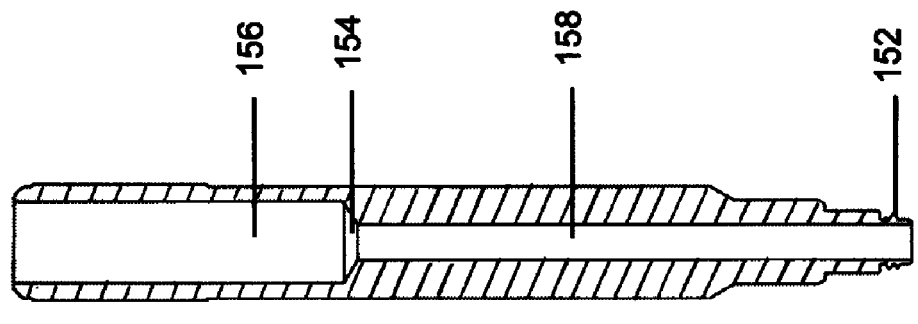
FIG. 4 is a longitudinal section view of the drill guide of FIG. 3.
Figure 3:
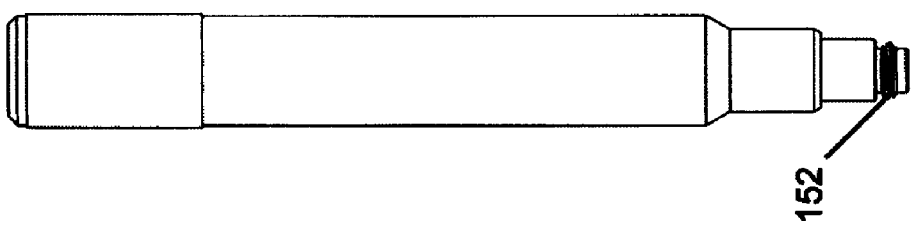
FIG. 3 is a side elevation view of a drill guide of the jig assembly of the invention.

Referring to FIGS. 1, 3 and 4, the jig assembly 100 further includes a drill guide 150 having a threaded end 152 which is positionable within the openings 114, 116 in the second portion 106 of the jig 102 and threadably engageable within the peg holes 40, 42, 44. The drill guide 150 preferably includes a stepped bore 154 having a larger diameter upper portion 156 and a smaller diameter lower portion 158. The lower portion 158 accommodates a drill bit appropriately sized for drilling a hole into bone for a peg 46, while the upper portion 156 accommodates a movable scale of a prior art depth gauge (not shown) for measuring the depth of a drilled hole and determining the location and depth of the drilled hole relative to particular anatomical structure. The drill guide 150 may be moved from one peg hole to the next to drill the required holes.

Turning now to FIG. 5, a second embodiment of a jig assembly 200 is shown. An upper first portion 204 of the jig 202 of the assembly 200 includes a plurality of longitudinally displaced circular holes 210, 212, 214, and slots 216, 218, 220 which provide lateral entrance into each of the holes. The slots 216, 218, 220 are preferably non-radial, and more preferably oriented parallel to both a radius and a tangent of the respective holes. A drill bit 260 may be side loaded into the holes 210, 212, 214 via the slots 216, 218, 220, without the use of a sleeve. The handle alone guides the bit, and the location of the slots relative to the holes operates to facilitate retention of the drill bit when the bit is rotated in a counterclockwise direction. This construction speeds use of the jig, as the drill bit 260 may be rapidly moved into and out of holes 210, 212, 214. After the holes are drilled into the bone, a driver (not shown) for the screws 26, 28 (FIG. 1) likewise can be inserted into the 210, 212, 214, with the screws manually positioned beneath the jig 202 and engaged by the driver.

Referring to FIG. 6, in the lower portion 206 of the jig 202, two opposite side openings (recesses) 214, 215 are provided which provide access to peg holes 40, 42 (see FIG. 1) in the fixation device 10a therebeneath, and a relatively distal bounded opening (hole) 216 is provided for access to a distal peg hole 44 (also in FIG. 1). The side openings are preferably symmetrical so that the jig 202 may be used with both left and right hand fixation devices 10a, as the left and right hand models will have oppositely directed pegs in corresponding peg holes 40, 42. In FIG. 5, drill guides 150 are shown coupled in each of the peg holes, though a single drill guide may be used and moved between the peg holes as holes are drilled in alignment with each. A hole 208 is also provided for receiving a locking screw 120 to couple the jig 202 to the fixation device 10a. Fixation device 10a and 10 (FIG. 1) are substantially the same with the exception that device 10a includes three cortical screw holes 22a, 24a, 25a, and device 10 includes only two such holes 22, 24.

Figure 7:
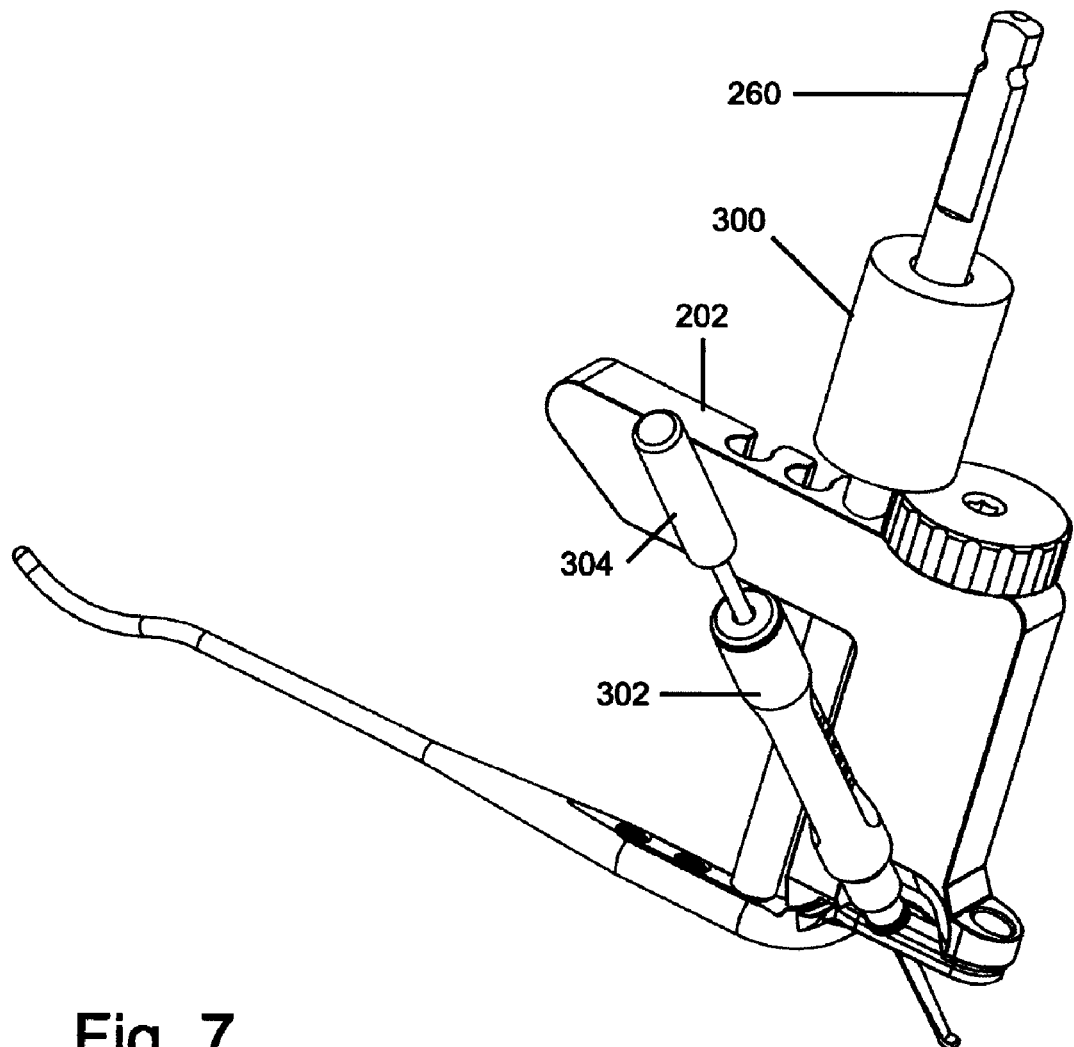
FIG. 7 is a first side perspective view of a further embodiment of a jig assembly and fracture fixation system according to the invention.
Figure 8:
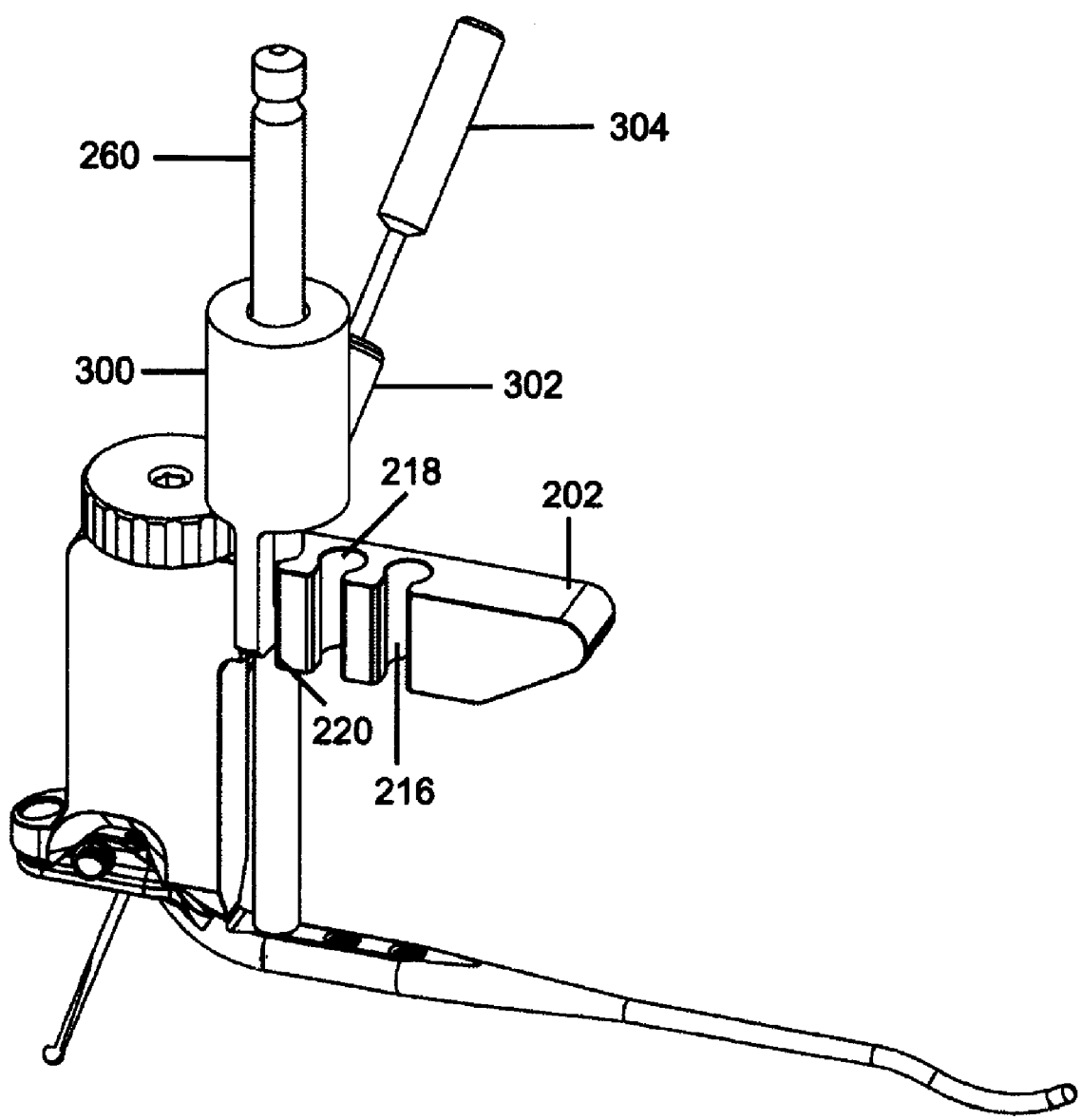
FIG. 8 is a second side perspective view of the jig assembly and fracture fixation system shown in FIG. 7.
Figures 9, 10:
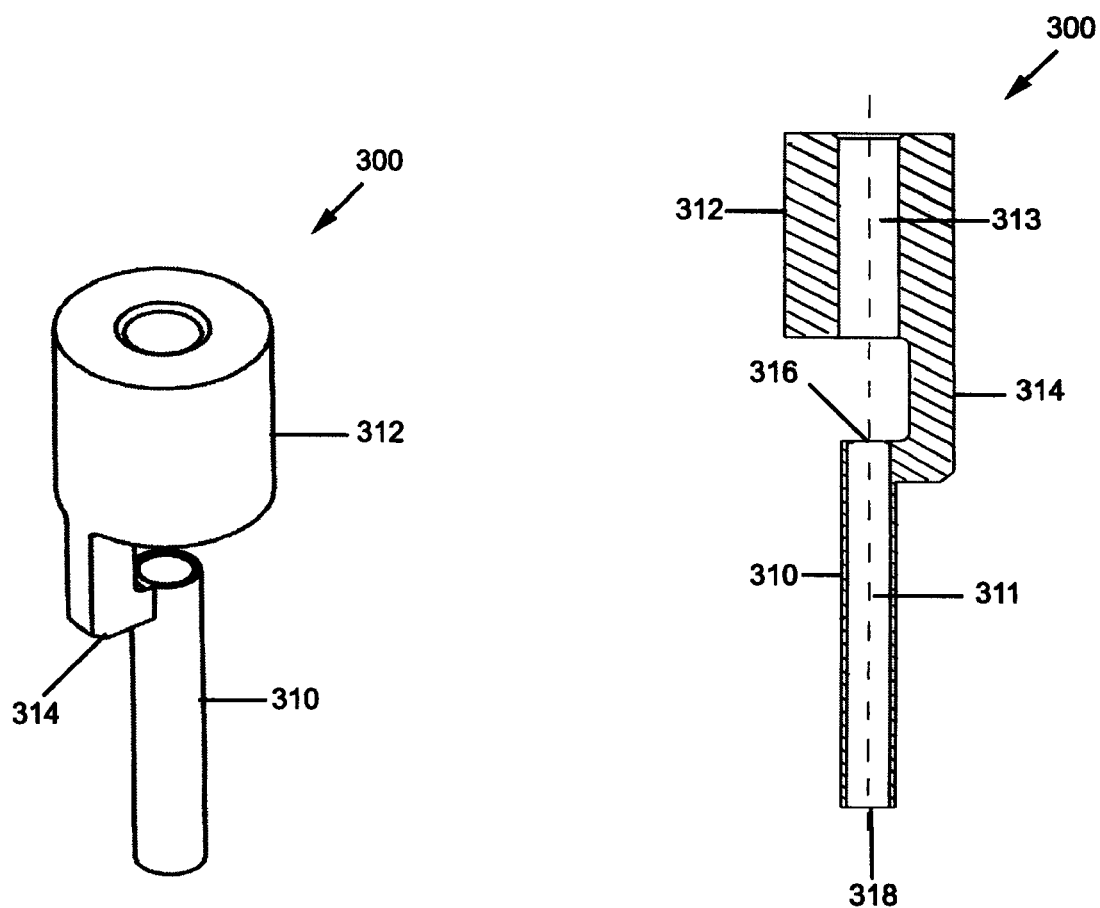
FIG. 9 is a perspective view of a guide sleeve according to the invention.
FIG. 10 is a longitudinal section view of the guide sleeve of FIG. 9.
Figure 11:
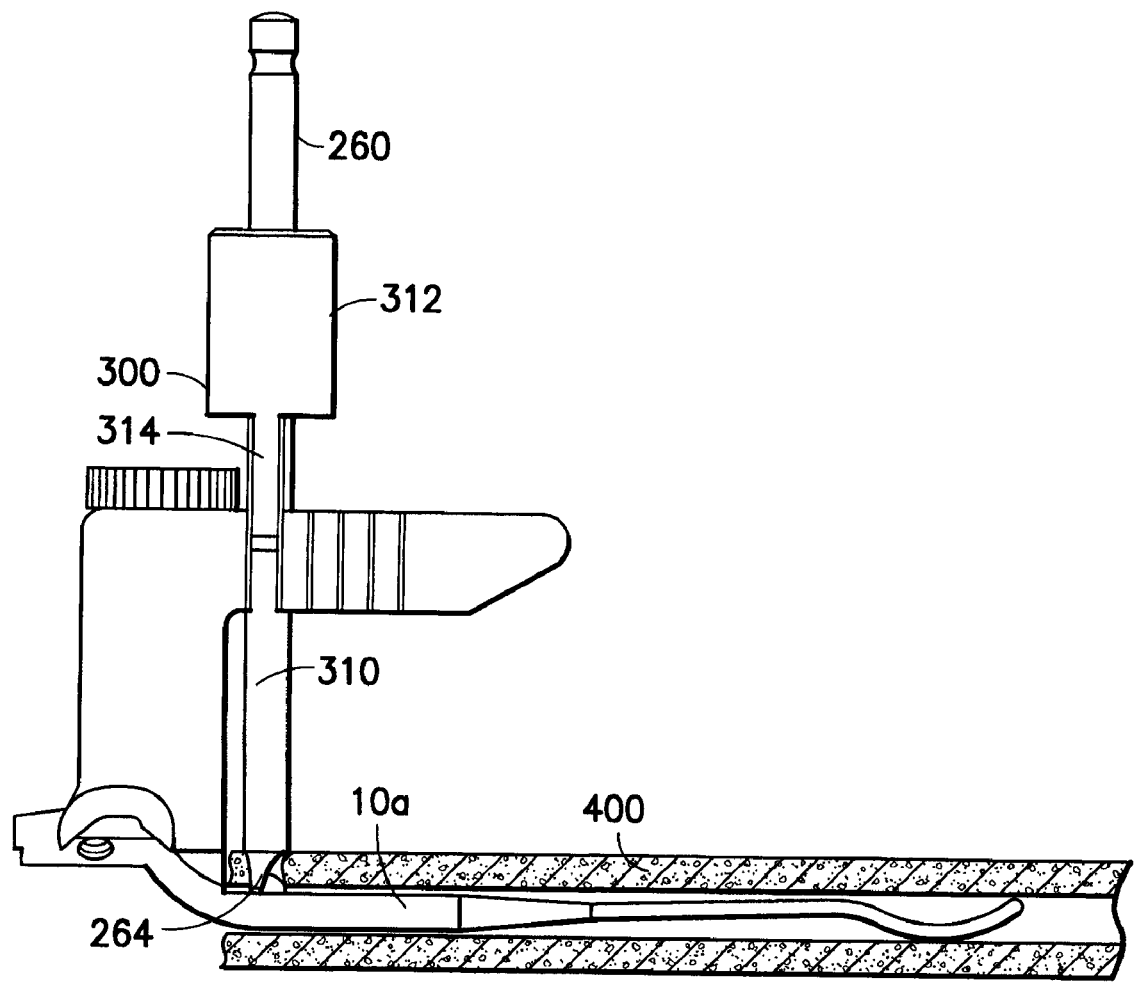
FIG. 11 is a side elevation of the jig coupled to an implant, with a bridged sleeve guiding a drill bit into a relatively thick radius bone.
Figure 12:
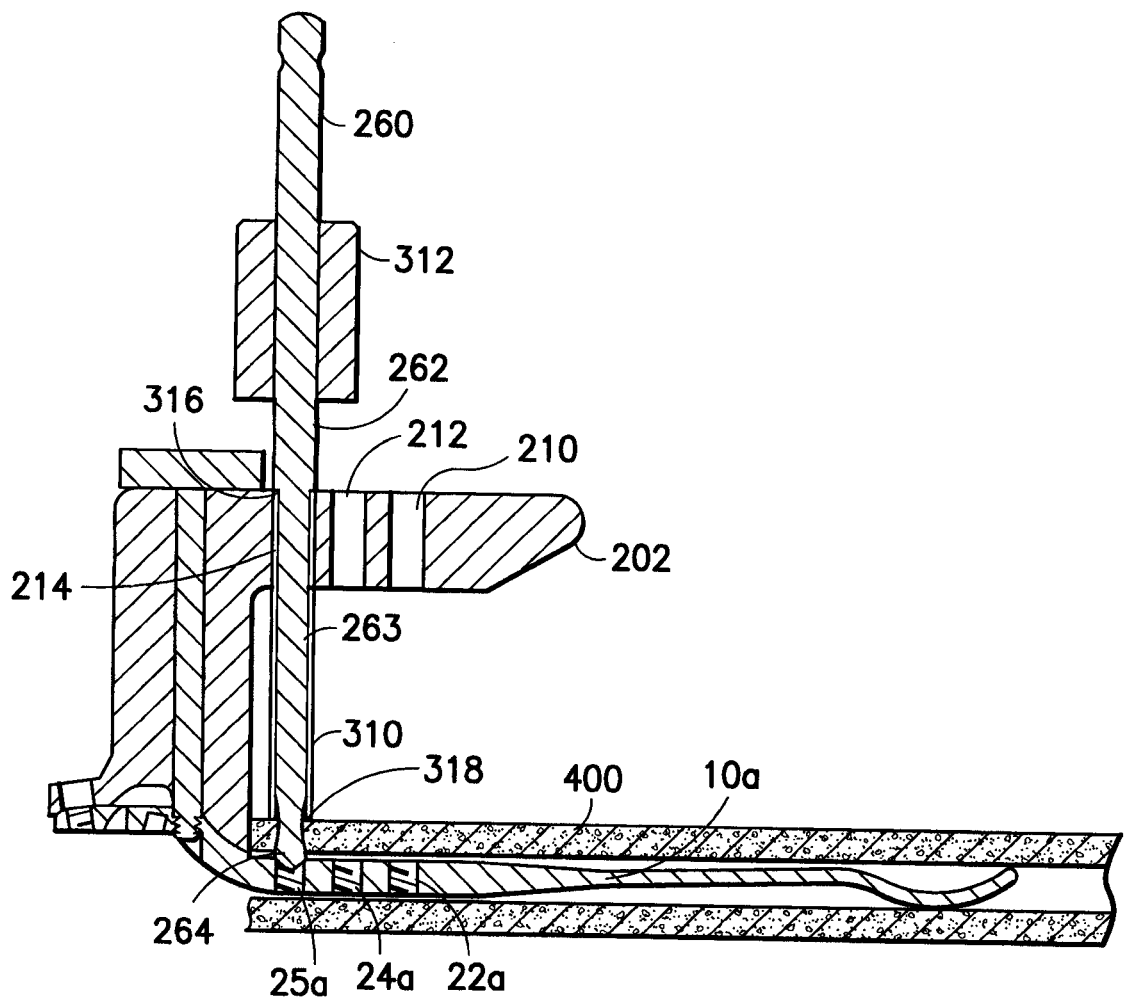
FIG. 12 is a longitudinal section view of the same elements shown in FIG. 11.

Turning now to FIGS. 7 and 8, according to another embodiment of the invention, the jig 202 is shown with a bridged-drill sleeve 300 extending over the drill bit 260, and an alternate drill guide 302 provided with a novel depth gauge 304. Referring specifically to FIGS. 9 and 10, the bridged-drill sleeve 300 includes a tube 310 defining a passage 311, and an upper bearing 312 having a bore 313 coaxial with the passage 311. A bridge 314, laterally displaced from the axes of the tube 310 and the bearing 312, couples the tube 310 and bearing 312 in a spaced apart relationship.

Referring now to FIGS. 9 through 12, the bore 313 of the bearing 312 has a relatively large first inner diameter sized to receive a proximal shoulder portion 262 of the drill bit 260. The passage 311 has a second inner diameter sized to stably receive and guide a relatively smaller distal portion 263 of the drill bit 260.

The shoulder portion 262 of the bit 260 is too large to fit through the circular holes 210, 212, 214 in the upper first portion 204 of the jig 202, and thus when the bit 260 is advanced through the jig, the shoulder portion 262 will abut the top surface of the first portion 204 of the jig 202 and stop the drill tip 264 at a predetermined distance relative to the jig 202, regardless of the thickness of the radius bone 400.

Figure 13:
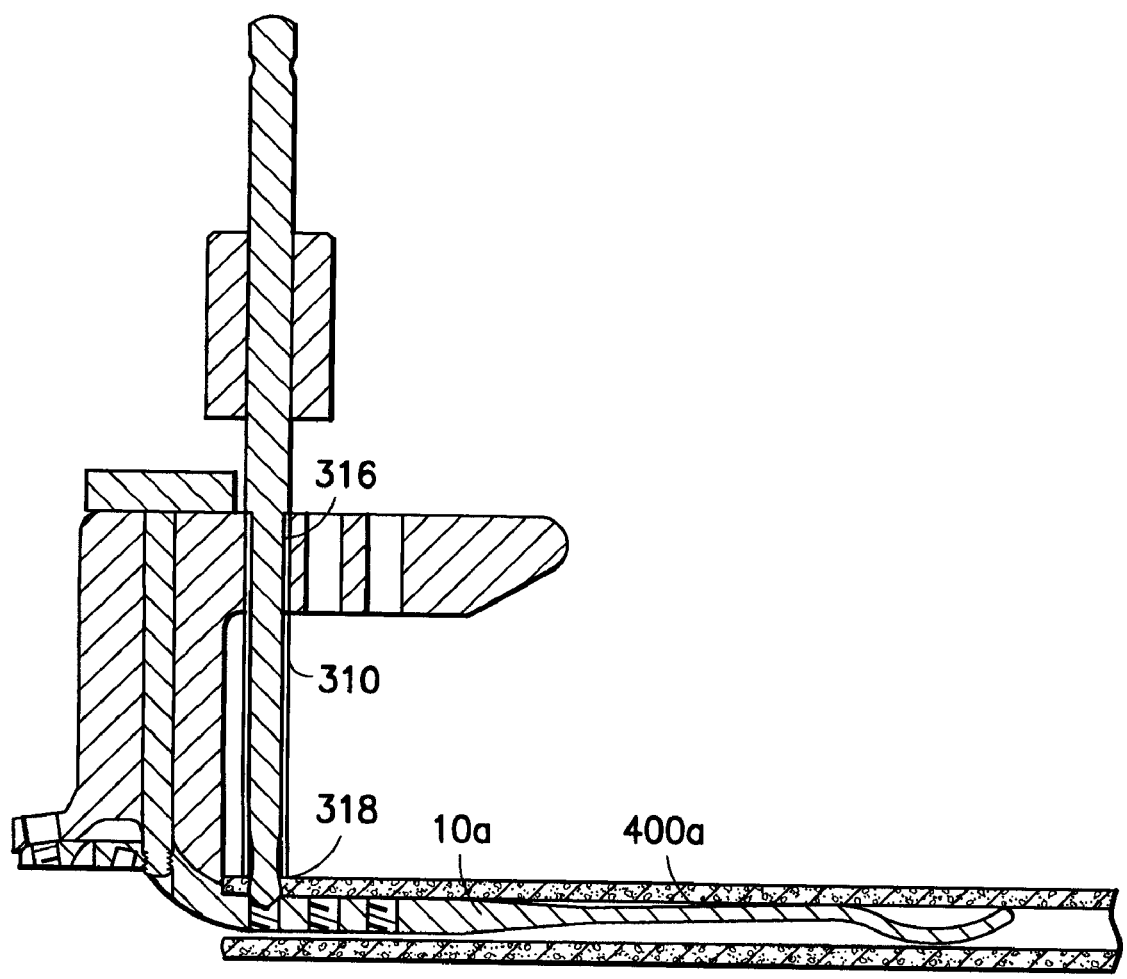
FIG. 13 is a longitudinal section view similar to FIG. 12 but where the radius bone is relatively thinner.

The bridge 314 is sized to be at least partially received within a slot 216, 218, 220 of the jig 202 (see FIG. 8) and the tube 310 is sized to be received within a hole 210, 212, 214. In order to guide the bit 260 to drill through different thicknesses of the radius bone (either a varying thickness of one bone beneath the holes 210, 212, 214 or in radius bones of various patients), the tube 310 and bridge 314 may slide up and down through a respective hole and slot relative to the jig. Based upon the thickness of the radius bone 400 on which the bottom 318 of tube 310 is positioned, the top end 316 of the tube 310 and bridge 314 will be located at a variable vertical location relative to the jig 202 while still operating to stably guide the drill bit 260 toward a hole 22a, 24a, 25a in the implant 10a. For example, compare the location of the top end 316 and bottom end 318 of the tube 310 in FIGS. 11 and 12, where the implant 10a is positioned within a radius bone 400 having a relatively thicker cortex, to the location of the top end 316 and bottom end 318 of the tube 310 in FIG. 13 where the implant 10a is positioned within a radius bone 400a having a relatively thinner cortex. Thus, the jig 202 with bridged sleeve 300 stably guides the drill bit toward screw holes in an implant regardless of the thickness of the radius bone.

The sleeve also has other advantages. The relatively massive size of the bearing 312 improves stability of the guide. The placement of a portion of the bridge 314 within a slot 216, 218, 220 of the jig 202 prevents the bridged sleeve 300 from rotating relative to the jig when the drill bit 260 is rotated. Further, the bottom end 318 of the tube 310 when positioned on the radius bone 400 prevents the drill tip 264 from catching and tearing non-bone tissue near the entrance to the drilled cortical bone.

Referring to FIG. 14, the drill guide 302 includes a threaded end 320 for threaded engagement with a peg hole of the fixation device 10a, and a relatively constant diameter bore 322. A window 324, open to the bore 322, is defined on each of two diametrically opposite sides of the drill guide 302. Graduated indicia 326 corresponding to a scale is provided along the sides of the windows 324. In a preferred embodiment, the indicia 326 correspond to millimeters and more particularly provide graduated indications of a depth of 14 mm to 30 mm, as measured relative to the tip 334 of a gauge 304 (FIGS. 15 and 16).

Referring to FIGS. 15 and 16, the gauge 304 includes a handle portion 326, a shaft 328 insertable through the bore 322 and having a reference mark 330 thereon, and an end portion 332. The reference mark 330 is clearly identifiable and preferably engraved or etched on the shaft 328, though it may also be applied or provided through other means such as, e.g., paint, oxidation, enamel, or a raised ridge or other mark.

The end portion 332 of the gauge is slightly angled relative to the remainder of the shaft 328, e.g., by approximately 3° to 6°, and most preferably 4.3°. The end portion 332 is spring-like in that if it is radially deformed from its pre-set angle relative to the shaft 328 it will return to the pre-set angle once the deformation force is removed. The end portion 332 includes a rounded tip 334 which ensures that the gauge rides smoothly in and out of drilled bone and bore 322 of the drill guide, and an angled upper catch 336, preferably angled at approximately 105° relative to a longitudinal axis through the end portion 332. The angle of the upper catch allows a user to retrieve the gauge without chipping bone, which may occur with a prior art gauge having a right-angle ledge. The end portion 332 preferably also slightly tapers in a lateral direction. Where the gauge is intended for use in conjunction with fracture fixation implants designed for the distal radius, the end portion 332 preferably has a length between approximately 10 mm and approximately 25 mm, and more preferably approximately 15 to 18 mm, and the diameter of the end portion is preferably less than approximately 3 mm, and most preferably approximately 1.5 mm. Other dimensions may be provided where the gauge is used in conjunction with orthopedic implants intended for other bone fractures.

When the drill guide 302 is coupled to a fixation device at a peg hole, the depth of a hole drilled therethrough may be measured by removing the drill and inserting the gauge 304. The end portion 332 and shaft 328 of the gauge 304 are fed through the bore 322 such that the end portion 332 is resiliently radially inwardly bent against the preformed angle by the relatively narrow diameter of the bore. Once the rounded tip 334 of the drill guide exits the far end of the drilled hole, the end portion 332 springs back such that the angled upper catch 336 catches on the far cortex of the bone. The depth of the hole (or size or length of an appropriate size bone peg) is measured (or otherwise determined) by the location of the reference mark 330, which is viewed through the window 324, relative to the indicia 326 on the drill guide 302. The measurement determines the size of the peg which will be inserted into the peg hole. After measurement, the gauge 304 is withdrawn from the drill guide 302. During withdrawal, the obliquely angled catch easily releases from the bone and the rounded tip 334 advantageously does not drag or scrape through the drilled hole. The process is repeated for each bone peg hole.

Figure 17:
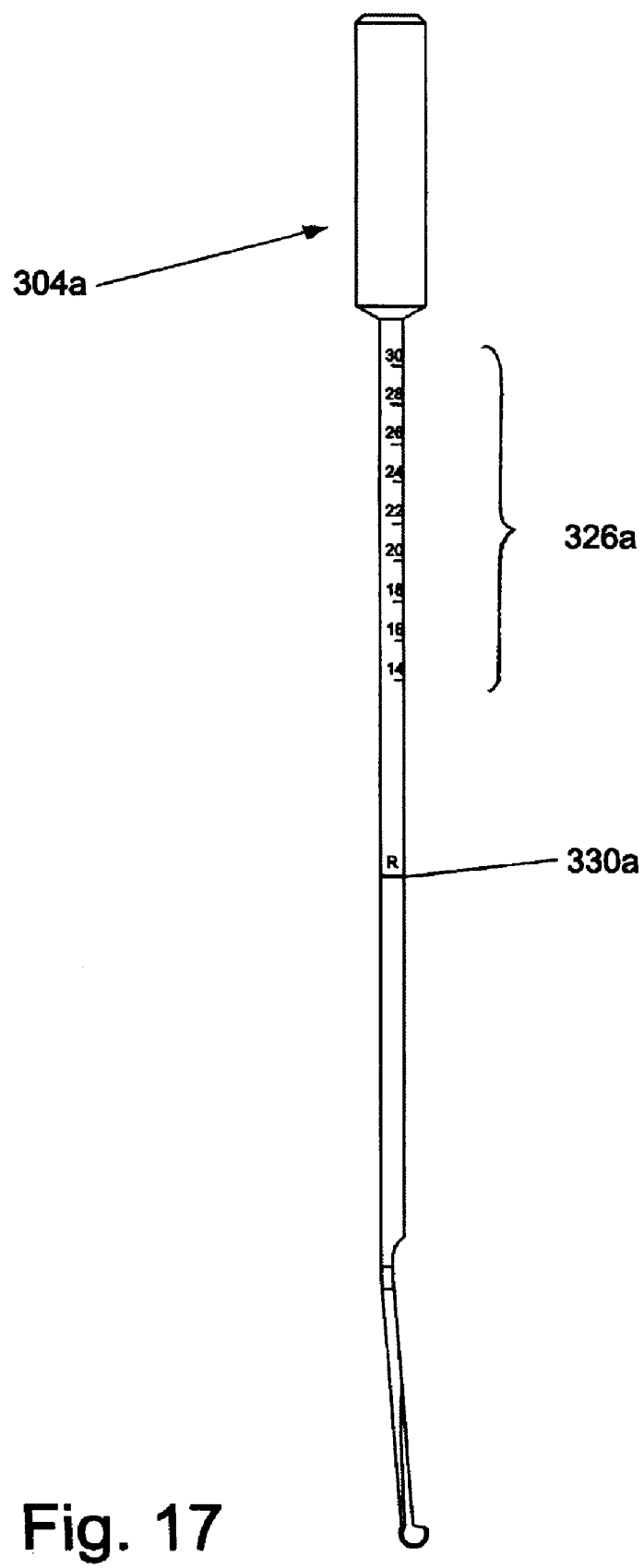
FIG. 17 is a view similar to FIG. 16 of an alternate embodiment of the gauge.

Referring to FIG. 17, additionally or alternatively, the gauge 304a may be provided with graduated indicia 326a corresponding to a scale (and may or may not include the reference mark 330a) so as to also be used with a conventional drill guide which does not have a window while still providing the advantages of gauge 304. In such case, the measurement of the drilled hole is read by referencing the top of the conventional drill guide against the scale provided by the indicia 326.

There have been described and illustrated herein embodiments of a jig assembly for implantation of a fixation device. While particular embodiments of the invention have been described, it is not intended that the invention be limited thereto, as it is intended that the invention be as broad in scope as the art will allow and that the specification be read likewise. Thus, while particular dimensions and angles have been disclosed, it will be appreciated that other dimensions may be used as well. In addition, elements of one embodiment may be combined with elements of another embodiment. For example, and not by way of limitation, the drill guide 302 may be used in place of drill guide 150 in all embodiments. It will therefore be appreciated by those skilled in the art that yet other modifications could be made to the provided invention without deviating from its spirit and scope as claimed.

What is claimed is:

1. A gauge system for use with an orthopedic implant and measuring the depth of a hole drilled into bone, comprising:
   a) a drill guide having a bore, a side window open to said bore, graduated indicia provided along a side of said window, and a threaded end for engagement with the orthopedic implant; and
   b) a gauge removable from said drill guide, said gauge having an elongate shaft portion provided with a reference mark, said shaft portion has an end portion angled by an angle relative to an adjacent straight portion of said shaft, said reference mark provided on said straight portion, and said end portion resiliently bendable relative to said adjacent portion,
      wherein when a hole is drilled using said drill guide and said gauge is inserted through said bore of said guide and into the hole, said angle is reduced and a depth through or within the hole is measured by the location of the reference mark, as viewed through said window, relative to said graduated indicia.

2. A gauge system according to claim 1, wherein:
said drill guide includes two windows located on diametrically opposite sides of said drill guide.

3. A gauge system according to claim 1, wherein:
said bore has a constant diameter.

4. A gauge system according to claim 1, wherein:
said angle is 3° to 6°.

5. A gauge system according to claim 1, wherein:
said end portion includes a rounded tip having an upper catch.

6. A gauge system according to claim 5, wherein:
said end portion tapers in a lateral direction at and adjacent said rounded tip.

7. A gauge system according to claim 5, wherein:
said upper catch comprises a surface obliquely angled relative to a longitudinal axis through said end portion.

* * * * *